United States Patent [19]

Klawitter

[11] 4,328,592

[45] May 11, 1982

[54] HEART VALVE PROSTHESIS

[75] Inventor: Jerome J. Klawitter, New Orleans, La.

[73] Assignee: Hemex, Inc., Austin, Tex.

[21] Appl. No.: 111,488

[22] Filed: Jan. 14, 1980

Related U.S. Application Data

[63] Continuation-in-part of Ser. No. 64,401, Aug. 7, 1979, abandoned.

[51] Int. Cl.³ .............................................. A61F 1/22
[52] U.S. Cl. ..................................... 3/1.5; 137/512.1; 137/527.8
[58] Field of Search ................. 3/1.5; 137/512.1, 527, 137/527.8

[56] References Cited

U.S. PATENT DOCUMENTS

| | | | |
|---|---|---|---|
| 3,589,392 | 6/1971 | Meyer | 3/1.5 X |
| 3,903,548 | 9/1975 | Nakib | 3/1.5 |
| 4,078,268 | 3/1978 | Possis | 3/1.5 |
| 4,159,543 | 2/1979 | Carpentier | 3/1.5 |
| 4,178,638 | 12/1979 | Meyer | 3/1.5 |
| 4,178,639 | 12/1979 | Bokros | 3/1.5 |
| 4,254,508 | 3/1981 | Bokros | 3/1.5 |
| 4,276,658 | 7/1981 | Hanson et al. | 3/1.5 |

FOREIGN PATENT DOCUMENTS

| | | | |
|---|---|---|---|
| 2846299 | 5/1979 | Fed. Rep. of Germany | 3/1.5 |
| 1160008 | 7/1969 | United Kingdom | 3/1.5 |

*Primary Examiner*—Ronald L. Frinks
*Attorney, Agent, or Firm*—Fitch, Even, Tabin, Flannery & Welsh

[57] ABSTRACT

Double-leaflet heart valves having improved flow through the orifice defined by an annular valve body include a pair of leaflets which may be arcuate or flat in cross section. Guides protrude oppositely from the leaflets and are received in complementary depressions in the interior wall surface of a pair of standards which extend downstream from the annular valve body at generally diametrically opposite locations. The depressions are preferably elongated so that, as the leaflets pivot between the open and closed positions, the guides move from one end of the elongated depressions to the other. Eccentric pivot axes provide for quick response of the leaflets, and the location of the depressions in the standards moves the leaflets out of the annular valve body, reducing resistance to the free flow of blood therethrough.

18 Claims, 19 Drawing Figures

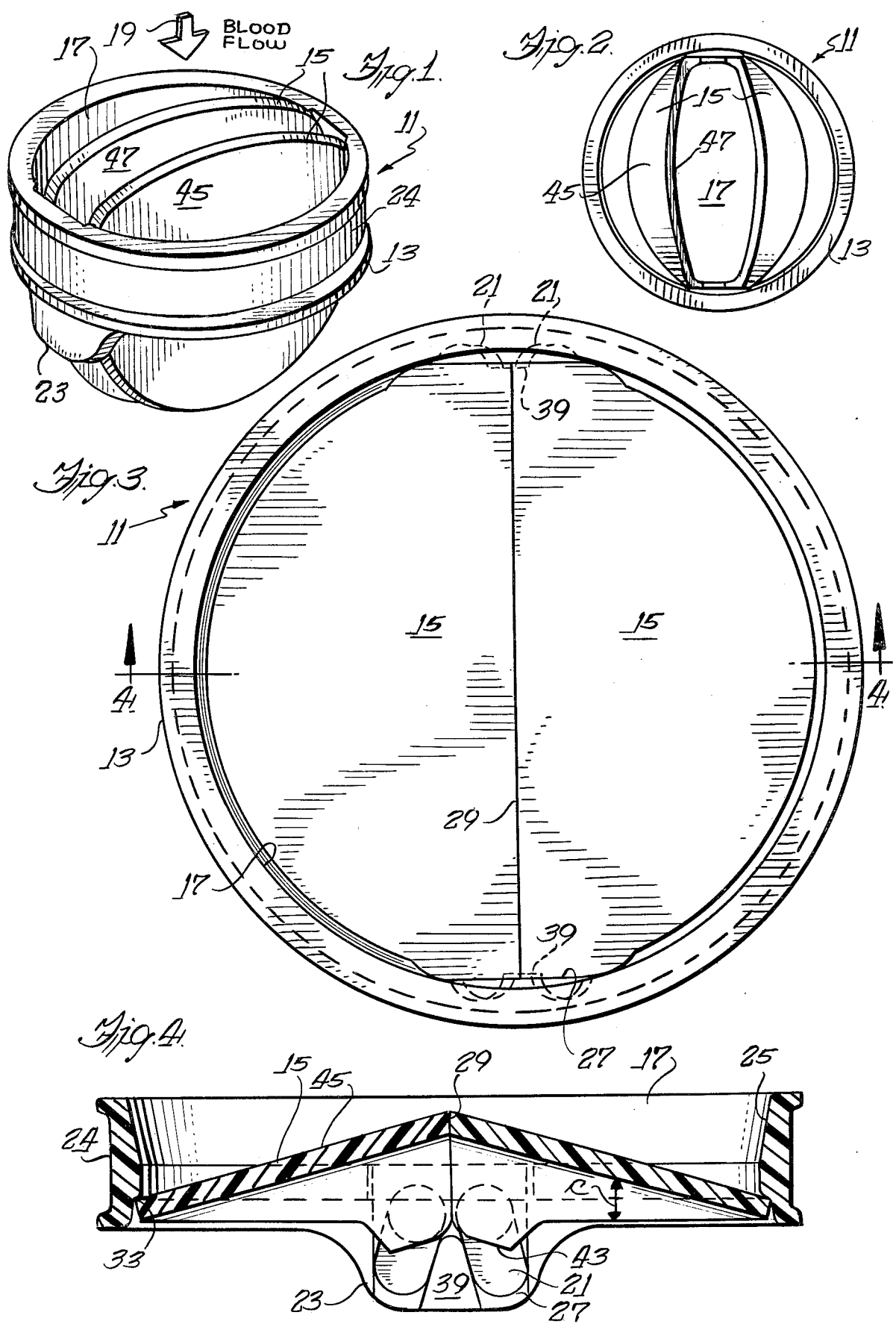

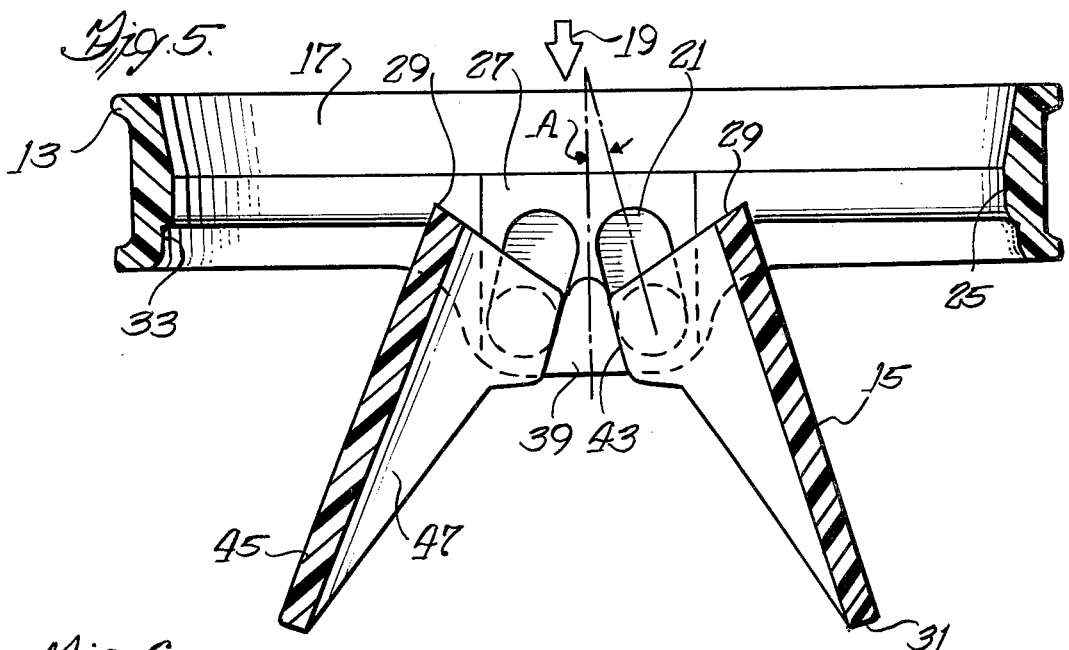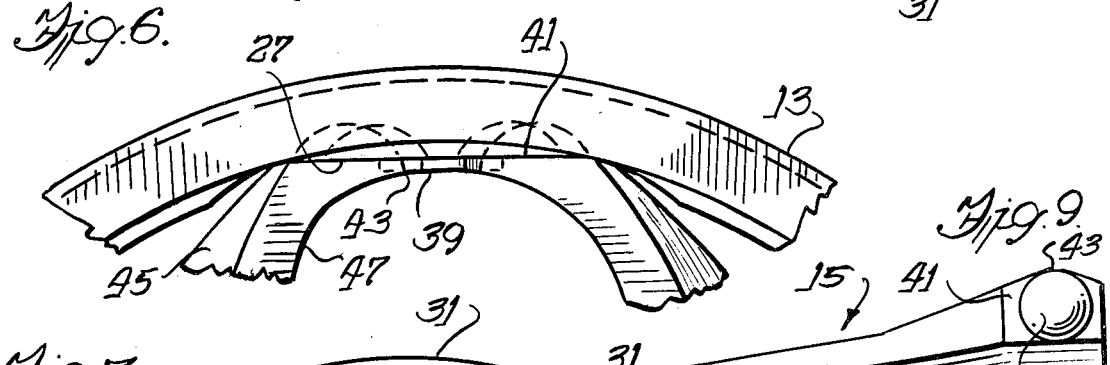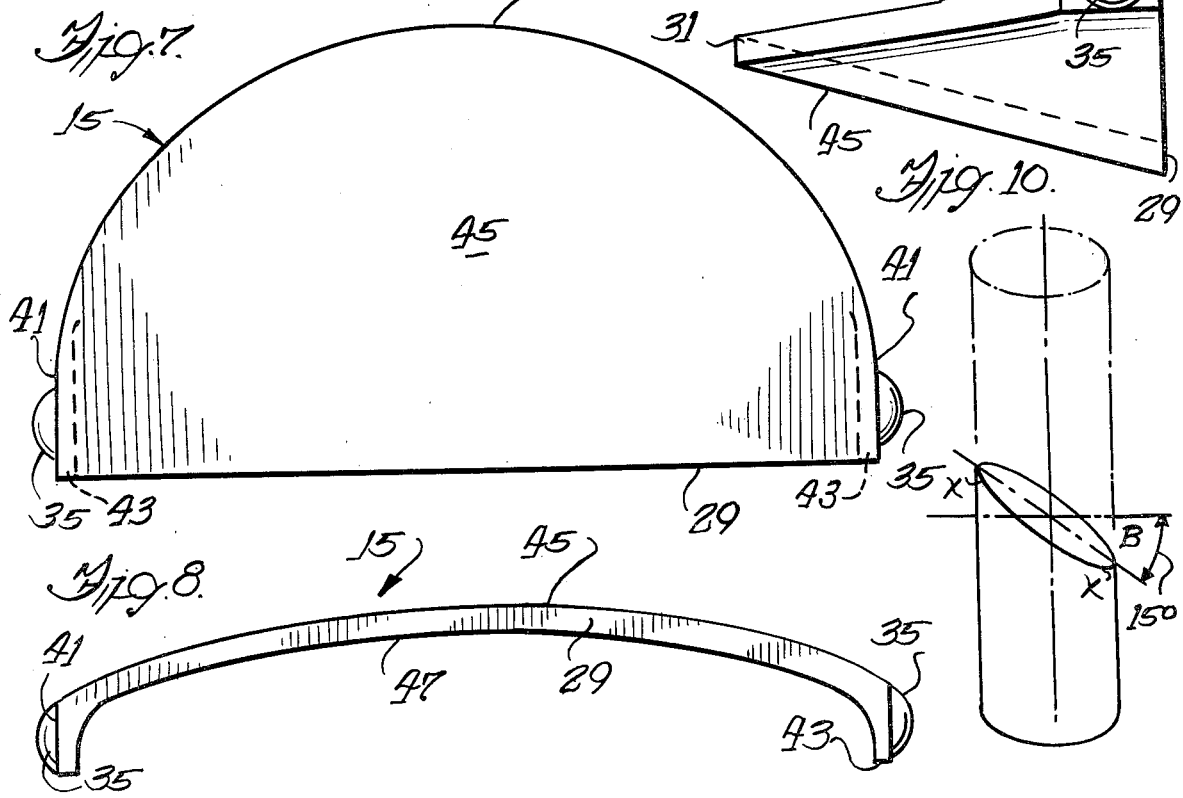

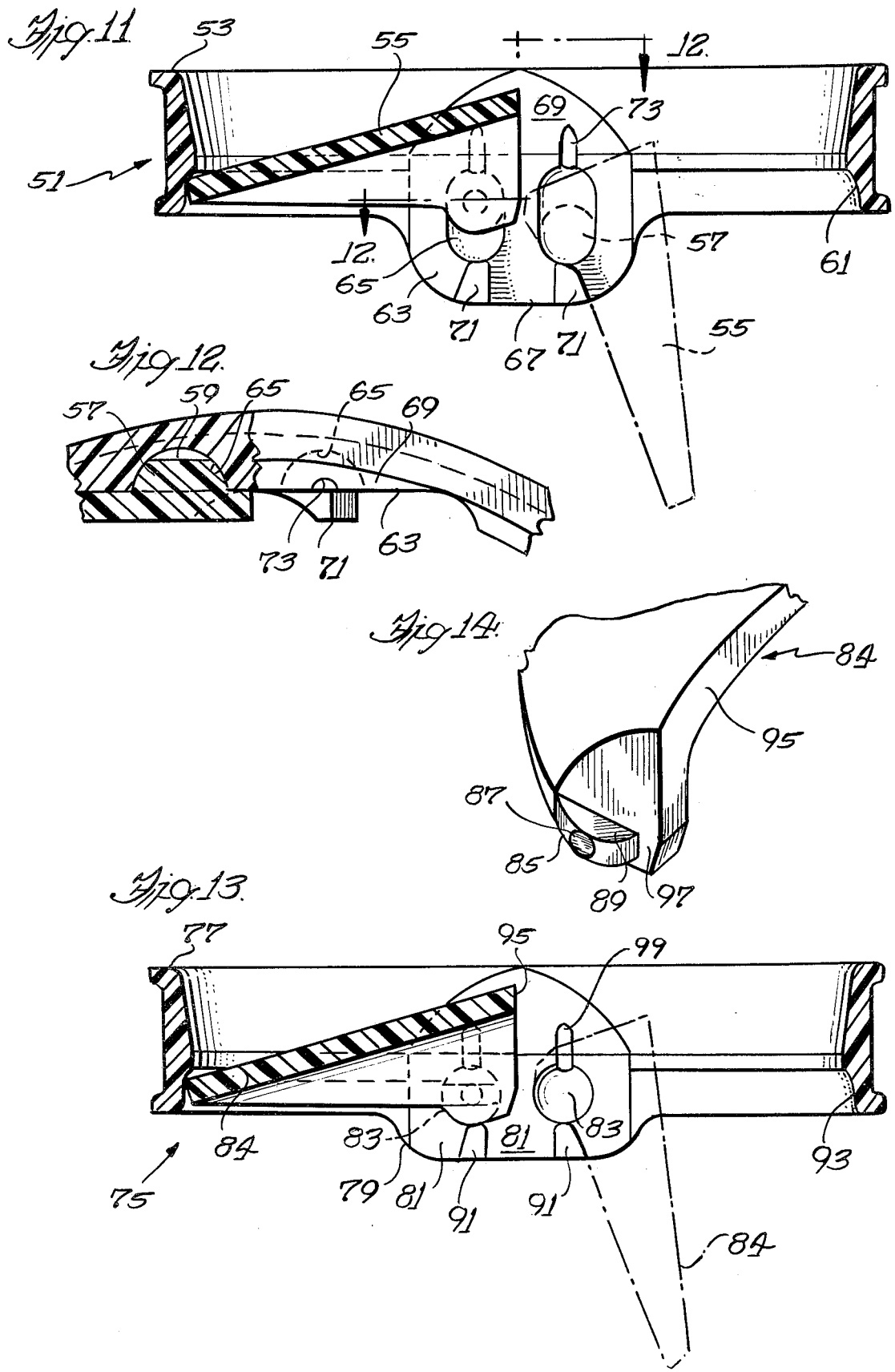

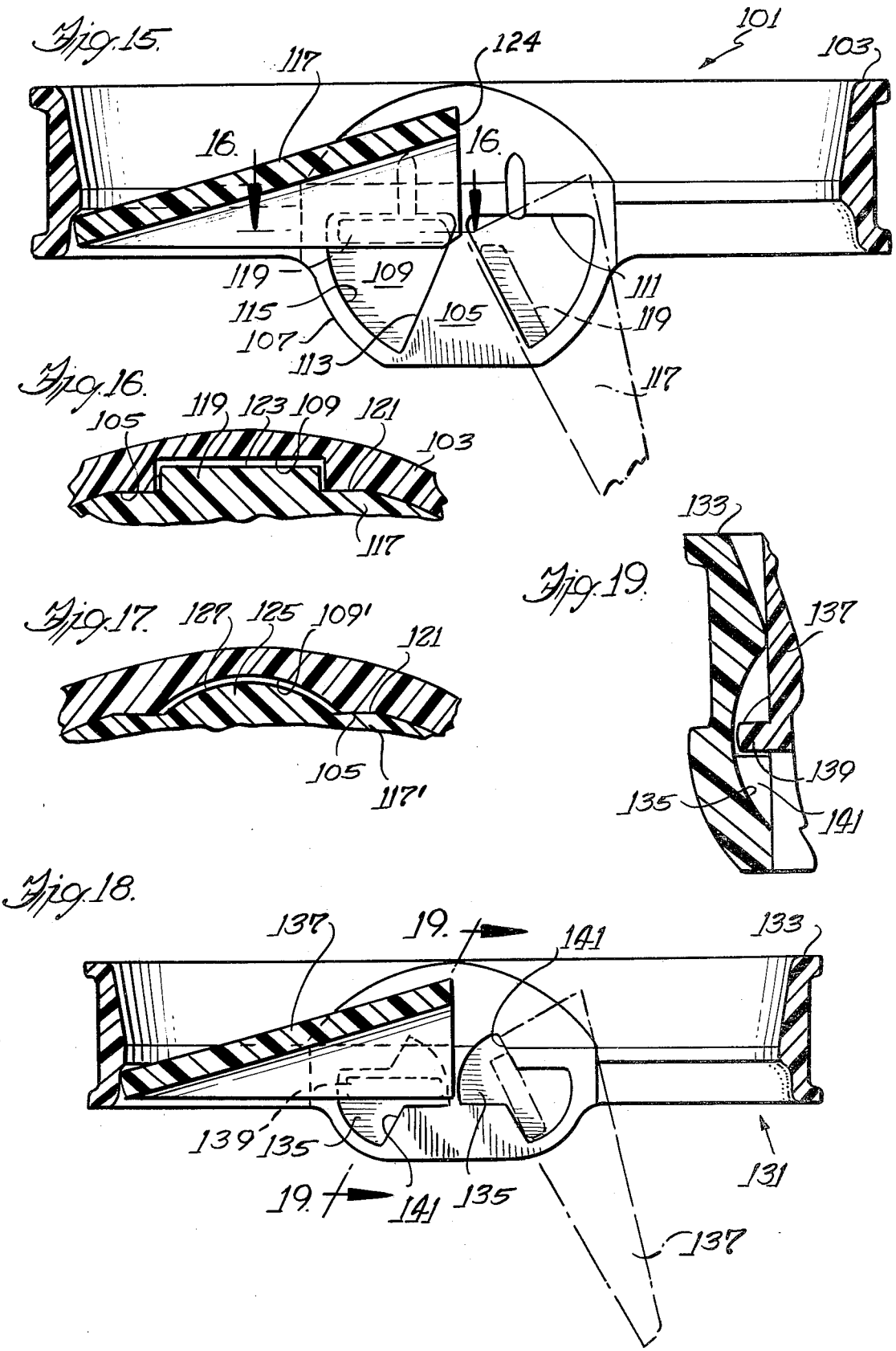

HEART VALVE PROSTHESIS

This application is a continuation-in-part of my copending application Ser. No. 64,401, filed Aug. 7, 1979.

BACKGROUND OF THE INVENTION

This invention relates to heart valve prostheses for replacement of defective natural valves and more particularly to heart valve prostheses using a pair of pivoting valve members, preferably ones which are arcuate in cross section.

Various types of heart valve prostheses have been developed which operate hemodynamically as a result of the pumping action of the heart. Some of these valves which have been used employ a ball-and-cage arrangement, whereas others have used a disc-type arrangement for the valve member. Exemplary of a disc of the free floating type is U.S. Pat. No. 3,534,411, issued Oct. 20, 1970. Various disc-type valves having a pivotal arrangement have been developed, such as that shown in U.S. Pat. No. 3,546,711 to Bokros, issued Dec. 15, 1970, and that shown in U.S. Pat. No. 3,859,668, issued Jan. 14, 1975.

Disc-type heart valves have also been developed which use two members or leaflets, instead of a single disc, which leaflets rotate about parallel axes as a part of the opening and closing of the valve. British Pat. No. 1,160,008 shows an early version of such a valve, and U.S. Pat. No. 4,078,268, issued Mar. 14, 1978, shows a later version.

SUMMARY OF THE INVENTION

The invention provides improved versions of two-leaflet heart valve prostheses having excellent blood flow characteristics. Guides extend from opposite sides of each of the leaflets and are received in depressions formed in the interior wall surfaces of a pair of standards which extend downstream from an annular valve body. The valve members are preferably curved in cross section, and each pivots about an eccentric axis. The depressions are preferably elongated or enlarged so that the axis of pivot of each leaflet changes relative to the valve body, and this movement in the depressions prevents blood clotting from beginning in an otherwise stagnant region. The location of the pivot axes slightly downstream of the orifice defined by the annular valve body, essentially removes them from the region of greatest constriction and provides the valve with excellent flow characteristics. When the valve members are curved, a fairly large central passageway is created which further enhances blood flow therethrough. The heart valves open and close easily and reliably and exhibit excellent resistance to wear.

BRIEF DESCRIPTION OF THE DRAWINGS

FIG. 1 is a perspective view of a heart valve embodying various features of the invention and having a pair of leaflets which are shown in the open position;

FIG. 2 is a plan view, reduced in size, of the valve of FIG. 1 shown in the open position;

FIG. 3 is an enlarged plan view showing the valve of FIG. 1 in the closed position;

FIGS. 4 and 5 are enlarged sectional views taken along the line 4—4 of FIG. 3, showing the valve in the closed and open positions;

FIG. 6 is a fragmentary plan view of the valve as shown in FIG. 5;

FIG. 7 is a view of one of the leaflets of the valve of FIG. 1 looking at the convex surface thereof;

FIG. 8 is a front view of the leaflet of FIG. 7;

FIG. 9 is a side view of the leaflet of FIG. 7;

FIG. 10 is a perspective view illustrating the curvature of the leaflet;

FIG. 11 is a sectional view, similar to the view of FIG. 5, of an alternative embodiment with the left-hand leaflet in the closed position and with the right-hand leaflet shown dotted in the open position;

FIG. 12 is a fragmentary, partial sectional view of the valve taken along line 12—12 of FIG. 11;

FIG. 13 is a sectional view of another alternative embodiment, similar to the view of FIG. 11, showing the left-hand leaflet in the closed position and the right-hand leaflet in dotted lines in the open position;

FIG. 14 is an enlarged fragmentary perspective view of the leaflet shown in FIG. 13;

FIG. 15 is a sectional view of still another alternative embodiment, similar to the view of FIG. 11, with the left-hand leaflet being shown in the closed position and with the right-hand leaflet shown dotted in the open position;

FIG. 16 is an enlarged fragmentary sectional view taken generally along line 16—16 of FIG. 15;

FIG. 17 is a view, similar to FIG. 16, showing yet another alternative embodiment;

FIG. 18 is a sectional view of a further alternative embodiment, generally similar to the view of FIG. 11, showing the left-hand leaflet in the closed position and the right-hand leaflet dotted in the open position; and FIG. 19 is a fragmentary sectional view taken generally along the line 19—19 of FIG. 18.

DETAILED DESCRIPTION OF THE PREFERRED EMBODIMENTS

Illustrated in FIGS. 1 through 9 is a heart valve 11 which has an annular valve body or housing 13 that carries a pair of pivoting leaflets or valve members 15 which hemodynamically open and close to control the flow of blood through a central passageway 17 in the direction of the arrow 19 (FIG. 1). The leaflets 15 are supported about eccentric axes in generally diametrically opposed depressions 21 formed in the interior wall of the annular valve body 13 and in the walls of a pair of standards 23 which extend in a downstream direction from the main ring portion thereof. The valve 11 can operate in any orientation and is not significantly affected by gravity; however, for ease of explanation, the valve 11 is shown and described with the annular valve body 13 being disposed horizontally.

The valve body 13 is formed with a peripheral groove 24 about its exterior surface that accommodates a suturing ring (not shown) which may be of any of the various types already well-known in the art. The suturing ring facilitates the sewing or suturing of the heart valve 11 to the heart tissue.

The passageway 17 through the valve body 13 is generally circular in cross section, and an internal wall 25 of the valve body defining the passageway 17 preferably tapers slightly in the upper region (see FIG. 4) and has a seat formed in the lower region as discussed hereinafter. The elongated depressions 21 are formed in flat or planar sections 27 of the internal wall 25 which continue down into the standards 23, and in this respect the passageway 17 deviates slightly from being perfectly circular in cross section.

The valve body 13 and the leaflets 15 are made of suitable material that is biocompatible and nonthrombogenic and that will take the wear to which it will be subjected during countless openings and closings of the leaflets. Preferably, the components may be made from isotropic polycrystalline graphite, such as that sold under the tradename POCO, which has been suitably coated with pyrolytic carbon, such as that marketed under the trademark PYROLITE, which gives excellent biocompatibility and wear-resistance.

The leaflets 15 are arcuate in transverse cross section (see FIG. 8) and may have a nominally uniform thickness along the upstream and downstream edges. They have the general shape of a section which has been cut from a tube of elliptical cross section. A minor edge 29 (which is the upstream edge of the leaflet 15 with respect to normal blood flow through the valve) is planar, and a major edge 31 (which faces downstream in the open position) preferably has the general shape of a portion of a semi-circle, i.e. to match the line along which it meets the inner surface of the generally cylindrical passageway 17. As can be seen from FIGS. 4 and 5, a horizontal seat 33 is formed in the interior wall 25, and the outline of the arcuate major edge 31 matches each nearly semi-circular portion of the seat 33. The elliptical curvature of each leaflet 15 is chosen so that the intersection between it and the right circular cylindrical interior wall surface 25 of the valve body 13 is substantially semicircular. The minor 29 and major 31 edges of the leaflets 15 are preferably appropriately shaped so that, in the closed position of the valve 11, the upper or upstream surface of the major arcuate edge 31 fits against the undersurface of the seat 33 and the minor planar edge surface 29 of one leaflet abuts against the similar planar edge surface of the other leaflet. The orientation of the seat 33 perpendicular to the centerline not only facilitates machining the seat, but also provides an excellent seal along the major part of the perimeter of the leaflets. The radius of curvature of the major edge 31 of the leaflet is such that there is line contact between it the seat 33 to reduce bloodcell crushing (hemolysis).

The pivotal axis for each of the leaflets 15 is eccentric to the leaflet and also to the centerline through the valve passageway 17, and it is defined by the location of a pair of oppositely extending guides 35 which are substantially spherical sectors. A spherical sector is that part of a sphere which is formed by a plane cutting the sphere, and the diameter of the sector is the diameter of the circle of intersection. The guides 35 are formed at opposite lateral locations on the arcuate leaflets 15 and are accommodated within elongated depressions or grooves 21 which have a radius of curvature, at the ends thereof, equal to or slightly larger than that of the spherical guides. The cross sections of the elongated depressions 21 have a similar radius of curvature that facilitates the pivotal and longitudinal movement of the guides. The leaflets 15 are each installed in the valve body 13 so its concave surface faces the centerline of the passageway 17 when in the open position (see FIG. 2).

The elongated depressions 21 are aligned somewhere between the vertical (i.e., parallel to the axis of the passageway 17) and at an angle A (FIG. 5) of not more than about 60° thereto extending outward in the downstream direction of blood flow. In the illustrated valve, angle A is equal to about 15°, and it preferably is not greater than about 45°. The distance across the valve passageway between the bottoms of the elongated concave surfaces of the depressions 21 is just slightly longer than the distance between the ends of the convex spherical surfaces of the guides 35, which provides sufficient clearance so the guides 35 can pivot and move freely therein. The material from which the valve body 13 and leaflets are made has sufficient resiliency to allow the leaflets 15 to be "snapped" or popped into operative position with the guides 35 received in the elongated depressions 21.

Each depression 21 preferably has a total length which is at least about 125 percent of the diameter of the spherical sector of the guides so that the movement of the guides 35 within the depressions coupled with the flow of blood therepast washes the entire concave surface of the depressions so that a positive deterent to clotting is provided. Although a longer depression could be used, the illustrated depressions 21 have a length equal to about twice the diameter of the sector and are adequate in providing complete washing. To assure freedom of movement, the radii of curvature of the opposite ends of the depressions 21 are preferably slightly greater than the radius of curvature of the guides 35.

The minor planar edges 29 abut and serve as a partial stop for the leaflets in the closed position; however, the primary stop is preferably provided where the arcuate downstream edges 31 of the leaflets abut the semi-circular seats 33 formed in the interior valve wall 25. The upper curved edge surface of the major edge 31 is in contact with the seat 33 along a line for substantially its entire length; the lateral edges of the seats 33 are cut away (see FIG. 6) so as to provide clearance for the leaflets in the regions near the guides 15.

Stops 39 are located in the regions between the depressions 21 to position the leaflets with their surfaces generally parallel to the axis of the central passageway 17 where they exert the least resistance to blood flow; however, the axes may be tilted slightly, i.e., up to about 25° for an aortic valve—with a tilt of 15° being shown in FIG. 5. Even if the leaflets, in the open position, are oriented precisely parallel to the axis of the passageway (i.e. at a 0° tilt), when blood flow through the heart chamber changes direction, the back pressure causes a backflow of the blood which exerts a dragging force on the curved leaflets 15 that is amplified by the composite moment arm (by which the major surface portion of the leaflet is offset from the pivotal axis of the leaflet) and quickly closes the valve 11. However, a 0° tilt requires maximum bolus of blood to move upstream to effect closure which undesirably increases regurgitation. Thus, the greater the tilt, the less the regurgitation, and the leaflets in a mitral valve may have a tilt as high as about 35°.

Depending upon the proportioning and the location of the protruding seats 33 and stops 39, each leaflet 15 may pivot between about 55° and about 75° in moving between its generally vertical orientation in the open position and the orientation in the closed position shown in FIG. 4. As earlier indicated, the curvature of the leaflets is preferably that of a part of an ellipse formed by a plane cutting a right circular cylinder at an angle B of about 10° to about 20°, see FIG. 10. The leaflet curvature as seen in FIG. 8 lies along the longer axis of the ellipse as indicated by the segment x—x of FIG. 10. This angle B is chosen is to match angle C in FIG. 4 which indicates the angle of reference between the surface of the leaflets 15 in the closed position and the plane perpendicular to the centerline of the valve passageway 17. The angle C is chosen to produce the desired orientation, i.e., preferably about 15°, in the heart valve 11. The diameter of the cylinder illustrated in FIG. 10 was selected with the diameter of the valve passageway in mind. Thus when the elliptical cross-section cylinder which the leaflet is patterned is cut by a plane at a specific angle C, it will produce a circle having the diameter of the valve passageway.

One example of a heart valve 11 designed for aortic location may have an outer diameter of about 24 millimeters and a central passageway 17 of about 21 millimeters in general diameter. The spherical guides 35 may extend about ½ to ¾ millimeter outward from the otherwise planar surfaces 41 on the opposite lateral sides of the leaflet, as best seen in FIGS. 7 and 9. As best seen in FIG. 8, the central portion of the curved leaflet 15 may have a fairly uniform thickness of about ¾ millimeter.

In the open position illustrated in FIG. 5, each leaflet 15 has swung downward to a position where it is substantially completely downstream of the annular valve body 13. The annular body constitutes the region of greatest restriction because, in the mitral position, the leaflets 15 will swing into the ventricle cavity and, in the aortic position, the leaflets enter an enlarged region just downstream of the entrance to the aorta. In the open position, the guides 35 have moved to the lower rounded ends of the depressions 21, further amplifying the displacement of the leaflets below the annular valve body.

During the opening movement of the leaflets 15, blood is flowing through the valve 11 in the direction of the arrow 19. For a valve in the aortic position, this occurs on the pumping stroke of the heart, as a respective ventricle contracts. Pivoting movement is halted when the rearward facing flat surfaces 43 on the leaflets contact the stops 39; however, because the tendency of blood flow is such to inherently orient the leaflets in a generally vertical position, there is little pressure exerted against the stops 39, and wear is not a problem. Because of their arcuate cross sectional shape and because the leaflets 15 have moved outward from the center as a result of the angle A of orientation of the elongated depressions 21, the main central passageway between the leaflets is quite large in size and allows free flow of blood therethrough. As earlier mentioned, the curvature of the tubular section which constitutes the leaflet 15 is preferably that of an ellipse formed by a plane which intersects a cylinder at an angle of between about 10° and about 20°, as illustrated in FIG. 10, and which is referred to as a 10° to 20° ellipse.

When, at the end of the stroke, the respective ventricle relaxes to draw more blood into the chamber from the atrium, the back pressure within the aorta causes the leaflets 15 to quickly swing or pivot to the closed position depicted in FIG. 4. Each leaflet 15 pivots about an axis which is defined by the spherical sector guides 35, and its construction is such that the drag of blood flow along the leaflet surface creates a force which acts through a significant moment arm causing a very prompt closing response. Because the center of gravity of each leaflet is located downstream of the axis when the leaflets are in the open position, pivoting occurs quickly as soon as backflow of blood begins. In the closing movement of the leaflets 15, the guides 35 move upward and slightly inward in the depressions 21, while the pivoting about the guides is occurring, until the major edge 31 of each leaflet 15 contacts the interior side wall 25 of the passageway 17 at the seat 33.

The more vertical the leaflets are in the open position and the longer the depressions 21, the greater will be the rotational movement of the leaflets in pivoting to the closed position and the greater will be the associated regurgitation. Therefore, the depressions 21 are preferably no longer than required for adequate washing, and the stops 39 are preferably formed to halt pivotal movement of the leaflets 15 as soon as they reach positions where the pressure drop through the valve in the open position is satisfactorily low, thereby limiting the amount of angular rotation that will take place during subsequent closing movement.

The upper surface of the major edge 31 is preferably rounded to a radius less than the radius of curvature of the underside of the seat 33 to maintain a line contact but still assure a seal occurs at this point. The leaflets 15 are preferably proportioned so that, when sealing contact has been established both along the abutting edge surfaces 29 and between the edge surfaces 31 and the seats 33, the guides 35 are displaced just slightly from the rounded upper ends of the depressions 21, thus unloading the interengaging pivot arrangements and lessening wear in this region.

As best seen from FIG. 6, the interior planar wall sections 27 of the valve body lie in close proximity to flat regions 41 formed on opposite lateral edges of the leaflets 15 in surrounding location to the guides 35. This proportioning of the leaflets 15 assures that the flat surfaces 41 move closely adjacent to the interior planar wall sections 27 as the leaflets pivot, and the arrangement provides adequate sealing in these diametrically opposite regions and prevents the leaflets from cocking and binding.

The curved leaflets 15, having the shape of a section of a tube of generally elliptical cross section, are each machined from a single piece of material, preferably polycrystalline graphite. As best seen in FIGS. 1 and 2, the outward facing surface 45 of the leaflet 15 is a convex surface, and the interior surface 47 of each leaflet is a concave surface. In the manufacturing process, the guides 35 are formed as sectors of a sphere of a desired radius, at the appropriate aligned locations at the opposite lateral sides of each leaflet, and thus define the eccentric axis about which the leaflet pivots. The guides 35 need not be an entire hemisphere but may be a spherical sector having a depth equal to about half the radius of the sphere. The guides could also be a sector of some other, generally spherical, surface of revolution, such as a paraboloid, a hyperboloid, or an ellipsoid. However, it is easiest to machine a spherical sector, and use of a spherical sector is preferred.

Following the machining of the spherical sector guides 35, the machining of the flat regions 41 surrounding the guides on the opposite lateral sides of the leaflets 15 is completed. Then, the minor planar edge 29 of the leaflet and the major semicircular edge 31 are machined, the convex surface 45 of each leaflet 15 being rounded at its major edge 31 to provide a radius of curvature which achieves a line contact with the underside of the stop 33 protruding from the valve body. After the entire machining process has been completed, the polycrystalline graphite leaflet substrate is coated with PYROLITE pyrolytic carbon to provide an integral, strong, wear-resistant, biocompatible surface about the entire exterior of the leaflet.

The elongated depressions 21 wherein the guides 35 travel have rounded ends which have a radius of curvature equal to or up to about 5 percent greater than the radius of curvature of the spherical guides, and preferably the radius of curvature is between about 1 and about 3 percent greater. The width of the depressions 21 is similarly between about 1 and about 3 percent greater than the diameter of the spherical sector. The total length of the depressions 21 illustrated in FIGS. 4 and 5 is equal to about twice the diameter of the spherical sector guide, and in general the depressions may have a length between about 125 percent and about 225 percent of the sector diameter. The elongated depressions 21 assure there is movement of the guides 35 back and forth therealong to prevent any stagnant region of blood from accumulating that could be the beginning of a clot; however, in view of the considerations previously mentioned, depression preferably has a length between about 125 percent and about 200 percent of the sector diameter.

In the illustrated embodiment, as best seen in FIG. 5, the elongated depressions 21 are aligned at an angle A of 15° to the vertical plane passing through the centerline of the valve passageway which is parallel to the eccentric axes of the leaflets. This angle A is preferably between 0° and about 45°, and accordingly the elongated depressions 21 may be aligned either vertical (i.e., directly downstream of normal blood flow) or at an angle downstream (i.e. laterally outward from the centerline of the valve body). The effect of the angle A being about 15° can be seen by comparing FIGS. 4 and 5. During opening movement, the leaflets move further outward from the center of the passageway 17 as they pivot into a generally vertical orientation, thus providing a larger central passageway through the valve, as depicted in FIG. 2, than if the depressions were either vertical, or not elongated. Inasmuch as the major portion of the blood flows through the central portion of the passageway, the outward movement of the leaflets 15 reduces the resistance to blood flow.

It can particularly be seen from FIGS. 4 and 5, that the valve body 13 has a very low profile, and this is considered to be a significant advantage in heart valve construction. It not only facilitates machining of the valve components, but it facilitates placement of the valve in the heart of the recipient. Because the annular valve body represents the region of greatest constriction, reduction of its height is felt to also keep the pressure drop at a minimum.

Illustrated in FIGS. 11 and 12 is a heart valve 51 which includes an annular valve body 53 and a pair of valve members or leaflets 55. The leaflets 55 are substantially the same as the leaflets 15 described hereinbefore except for the guides 57, which instead of being spherical sectors are spherical segments. A spherical segment is that part of a sphere which is formed by two parallel planes cutting the sphere, and thus each guide 57 has a flat circular end surface 59.

The annular valve body 53 has a pair of generally semi-circular seats 61 in opposed locations which are substantially the same as the seats 33, and the main difference lies in the diametrically opposed planar regions 63 where the guides are received. The annular valve body 53 again defines a generally circular passageway which tapers slightly from the upper end inward to the region of the seat 61. Elongated depressions 65 which receive the guides 57 are formed in the pair of opposed planar regions 63 which extend from a level just above the seat downward through the region of a depending standard 67. In the valve body 53, a slanted transition surface 69 extends from the upper edge, at the diametrically opposed locations, downward to each planar section and thus provides a smooth transition for the flow of blood past the planar regions 63.

The elongated depressions 65 are aligned substantially vertically, i.e., parallel to the centerline through the passageway. Thus, when the leaflets 55 pivot back and forth between the open and the closed positions, the changing axes of rotation do not move radially of the passageway, and the only movement of the axis is upstream and downstream.

A pair of stops 71 are provided which protrude from the bottom portion of the flat surfaces 63 and which are designed to limit the movement of the leaflets 55 in the open position to that illustrated in FIG. 11 in dotted outline. In this position, the leaflets 55 are oriented so that the axis of the curved major body portion is at an angle of about 5° to the vertical, which provides relatively little resistance to blood flow. As can also be seen from the dotted outline in FIG. 11, the leaflet 55 has moved downstream and nearly completely out of the region of the annular valve body in the open position, thus further reducing resistance to the flow of blood exhibited by the overall valve 51.

A small passageway or groove 73 is provided in the flat surface 63 above the depressions 65, and the groove also extends through the transition surface 69. The purpose of the groove 73 is to provide a controlled leak backward through the valve 51 during the time that the leaflets 55 are closed which is feasible because the volume of the depressions 65 is substantially larger than the volume occupied by the guides 57. The guides 57 will be in the upper portions of the elongated depressions when the leaflets 55 are in the closed position, as illustrated by the left-hand leaflet in FIG. 11, and the lower portion of the depression will be vacant and open to the pressure of blood on the underside of the leaflets. From FIG. 12, it is seen that blood can flow upward from the vacant lower portion of the depressions 65, past the circular surface 59 at the ends of the shortened guides and thence through the groove 73. This controlled backflow leakage through the four depressions 65 is quite tolerable in the valve design, inasmuch as an excellent seal is provided along the generally semi-circular edges at the seats 61. This backflow provides a repetitive flushing of the depressions 65 which constitutes a positive deterent to the beginning of any clotting in these regions.

Depicted in FIGS. 13 and 14 is a modified version of a heart valve 75 embodying various features of the invention which includes a valve body 77 generally resembling that shown in FIG. 11 with the exception of the depressions. The valve body 77 includes a pair of standards 79 which extend from the main ring portion of the annular valve body in a downstream direction. A pair of diametrically opposed flat sections 81 are provided in the valve body 77 which extend downward and constitute the inner surfaces of the standards 79. Formed in these flat sections 81 are a total of four depressions 83 each having a concave surface which is substantially that of a sector of a sphere.

Mounted in the valve body are a pair of leaflets 84 resembling the leaflets 55 as shown in FIGS. 11 and 12 but having a slightly modified pair of guides 85. Each of the guides 85 (see FIG. 14) has a surface that is a section of a spherical segment, i.e., in addition to being foreshortened at the tip to provide a circular end surface 87, both sides are also cut away to provide a relatively elongated protrusion which is defined by a pair of lateral parallel sides 89.

To position the valve leaflets 84 in the desired orientation in the open position, a pair of stops 91 are provided, which are essentially the same as the stops 71 illustrated in FIG. 12. The location and proportioning is such that the axes of the curved major body portions of the valve leaflets 84 are oriented about 10° to 20° from the vertical, as generally depicted in dotted outline in FIG. 13. The eccentric axis plus the drag on the surfaces of the curved leaflets 84, which have centers of gravity downstream of the pivot axes, provide a quick response to the change of blood flow and effects prompt closing of the leaflets with little regurgitation of blood.

As depicted in full lines in FIG. 13, the semi-circular edge of the leaflets 84 seals along a line upon the underside of a seat 93 in the annular valve body 77, and the planar surfaces 95 of the minor leaflet edge likewise abut each other, as in the embodiment described in detail with respect to FIGS. 1 through 10. In the closed position, the elongated guides 85 are positioned transverse to the centerline through the passageway. As earlier indicated, there will be some clearance between the flat sections 81 of the annular valve body and the planar lateral sides 97 at one end of each of the leaflets. There will also be clearance at the edges of the leaflets where the guides 85 protrude which allow blood to enter the depressions 83. Thus, a spurt of blood flows past the flat surfaces 87 and out the grooves 99 during each interval when the leaflets are closed and the back pressure builds up. This repetitive flow of blood cleanses the depressions 83 and prevents the beginning of clotting.

Although it is preferred to provide the depressions 83 in the flat internal walls 81 of the valve body 77 and to form the protruding guides 85 upon the lateral surfaces 95 of the leaflets, these parts could be reversed so that the depressions are cut in the lateral surfaces 97 of the leaflets and the protruding guides formed at appropriate locations on the opposed flat sections 81 of the valve body without departing from the invention. Similar reversal of parts could be effected with regard to the other embodiments described herein, including those which are hereinafter described.

Depicted in FIGS. 15 and 16 is still another modification of a heart valve prosthesis 101 which includes an annular valve ring 103, generally resembling the ring 53, wherein flat opposed sections 105 are provided which likewise extend downward and form the interior surfaces of the standards 107. Formed in each of these flat surfaces is a pair of depressions 109 which are generally pie-shaped, i.e., having the outline of a sector of a circle, with the apex located nearest the centerline of the passageway. An upper edge 111 of each of the depressions is oriented substantially perpendicular to the centerline, and the other straight edge 113 of the depression 109 serves as the stop in the open position. The lower edges 113 can be slightly longer than the upper edges 111 to provide for some movement within the depression in addition to the pivoting movement, and the circular edge 115 of the depressions 109 provides a guide surface for the movement as the leaflets 117 pivot from the closed to the open position.

Guides 119 protrude from the planar lateral surfaces 121 of the leaflets 117 and are elongated and have a length just slightly less than the length of the upper edges 111 of the depression, and the edges of the guides 119 are of course rounded. As seen in FIG. 16, the end surfaces of the guides 119 may be flat surfaces 123 which correspond to flat surfaces which form the walls of the pie-shaped depressions 109. The proportioning of the leaflet guides 119 is preferably such that the thrust bearing surface, during pivoting movement, is one of the flat end surfaces 121 of the leaflets against the flat sections 105. Accordingly, there is preferably a slight clearance between the end faces 123 and the flat interior wall 109 of the depressions 109. This clearance assures that, in the closed position, there is a slight backflow of blood through the depressions 109 and upward around and past the guides 119 so as to provide sufficient cleansing flow to avoid clotting. Alternatively, the guides 119 could be lengthened so as to bear against the flat surfaces 109 of the depressions. In pivoting from the open to the closed positions, the rounded ends of the guides 119 pivot at each apex of the depression until the planar edge surfaces 124 of the leaflets abut, when slight displacement occurs to remove force upon the guides 119.

Depicted in FIG. 17 is a slight modification of the valve shown in FIGS. 15 and 16. In the FIG. 17 embodiment, leaflets 117' are provided with elongated guides 125 which, instead of having a flat end surface, are generally segments of a circular disc, i.e., the end surface 127 is straight in its minor dimension and circular in its major dimension. The depressions 109' are of course formed with a complementary concave interior surface, which might have about a 1 percent greater radius of curvature to assure movement without binding. The rounded surfaces 109' and 127 serve to direct the pivotal movement, whereas the flat surfaces 105, 121 serve as the bearing surfaces. In this embodiment, the upper and lower edges of the depressions 109' are preferably the same length, to facilitate the ease in machining, and thus only pivotal movement occurs.

Depicted in FIGS. 18 and 19 is still another modified version of a heart valve 131 which resembles the FIG. 17 version just discussed; however, instead of having depressions which have a pie-shaped outline, the valve body 133 is formed with a pair of depressions 135 which have the outline of a pair of intersecting circular segments—an outline generally resembling that of a butterfly. The leaflets 137 are provided with guides 139 having an edge which is preferably circular, and thus the guides 139 can be essentially the same as the guides 125 depicted in FIG. 17 or the edge surfaces can be spherical sections.

The butterfly outline of the depressions 135 provides a pair of flat surfaces 141 which engage opposite flat surfaces of the guides 139 to position the leaflets in the desired orientation in the open position. Clearance can be provided between the ends of the guides 139 and the curved edges of the depressions 135 so as to permit a controlled leakage flow of blood therepast when the leaflets are closed and thus provide a positive deterrent to the formation of clotting therein. Instead of forming the guides 139 with the preferred circular edge, they could also be provided with a flat edge similar to that illustrated in FIG. 16, in which instance the butterfly depressions would have a flat interior wall.

All the illustrated designs use an annular seat which is preferably oriented with respect to the pivoting leaflets so that, at closure when pressure and force against the leaflets are at the maximum, the leaflet curved edges are in line contact upon the seat and the planar edges abut each other so that there is little force on the pivot guides. Because most wear occurs just at closure, wear is distributed along the seat and is not focused on the pivot guides.

Although the invention has been described with regard to a number of preferred embodiments which constitute the best modes presently known to the inventor, it should be understood that changes and modifications as would be obvious to one having the ordinary skill in this art may be made without departing from the scope of the invention which is defined solely by the appended claims. For example, although all of the leaflets have been described as having the preferred curved configuration, it should be understood that some of the advantages of the invention would still be obtained if flat leaflets were employed and that the use of such flat leaflets might be employed in the particular embodiments illustrated in FIGS. 11, 15 and 18 with only minor accompanying changes in construction. Of course, the use of flat leaflets does not provide the preferred wide flow path through the central portion of the passageways between the leaflets in the open position.

Particular features of the invention are emphasized in the claims that follow.

What is claimed is:

1. A heart valve prosthesis comprising an annular valve body having a central passageway therethrough designed to be mounted to permit the flow of blood therethrough in a predetermined downstream direction, and
   a pair of leaflets which are supported for substantially pivotal movement on eccentric axes between a closed position blocking blood flow through said central passageway and an open position allowing blood flow therethrough in said predetermined downstream direction,
   said annular valve body including a pair of substantially diametrically opposed standards extending from a main portion of said body in said predetermined downstream direction,
   said leaflets and said valve body including projecting guides and complementary depressions which receive said guides,
   said depressions and said projecting guides mounting said leaflets in a manner to allow pivotal movement relative to said annular valve body,
   either said depressions or said guides being located at least partially in said standards so that, in the open position, said leaflets are substantially displaced from the spatial region of said main portion of said annular valve body in a direction downstream of the flow of blood therethrough.

2. A heart valve in accordance with claim 1 wherein said guides each have a surface which is a portion of a spheroidal surface and wherein said depressions are formed with a surface of substantially mating curvature.

3. A heart valve in accordance with claim 2 wherein said projecting guides are carried by said leaflets and wherein two pairs of said depressions are located in said valve body at least partially in said standards.

4. A heart valve in accordance with claim 3 wherein each of said guides have a surface which is generally that of a spherical sector and wherein said depressions are elongated and extend downstream for a distance of at least about 125 percent of the diameter of said spherical sector and at an angle of between 0° and about 45° outward from a line parallel to the centerline of said central passageway.

5. A heart valve in accordance with claim 4 wherein said depressions extend in a subtantially straight line.

6. A heart valve in accordance with claim 1 wherein said leaflets are formed with a pair of substantially planar, substantially parallel lateral surfaces from which said guides protrude.

7. A heart valve in accordance with claim 6 wherein said guides are defined partially by a pair of substantially parallel side surfaces which are substantially perpendicular to said leaflet lateral surfaces.

8. A heart valve in accordance with claim 7 wherein said guides each include an end surface of generally spherical curvature.

9. A heart valve in accordance with claim 7 wherein said guides each include a flat end surface having rounded edges.

10. A heart valve in accordance with either claim 8 or 9 wherein said depressions each have a surface outline of the general shape of a pie-shaped circular sector with the apex of said sector located nearest the centerline of said central passageway.

11. A heart valve in accordance with claim 1 wherein said depressions are substantially larger in volume than the volume of said guides and wherein there is communication between said depressions and the bloodstream both downstream and upstream of said leaflets so that a controlled backflow of blood through said depressions occurs during the time said leaflets are in the closed position.

12. A heart valve in accordance with claim 11 wherein said depressions are formed in a pair of opposed flat interior surfaces of said annular valve body and wherein a groove is provided in said flat surfaces between each of said depressions and the central valve body passageway upstream of said leaflets.

13. A heart valve in accordance with claim 1 wherein each of said leaflets has a downstream edge which is substantially semicircular and wherein said valve body is formed with annular seat means having a downstream-facing surface against which said leaflet downstream edges abut in closed position.

14. A heart valve prosthesis comprising an annular valve body having a central passageway therethrough which is designed to be mounted to permit the flow of blood therethrough in a predetermined downstream direction, and
   a pair of leaflets which are supported by pairs of guides in opposed elongated depressions upon said annular valve body for substantially pivotal movement on eccentric axes between a closed position blocking blood flow through said central passageway and an open position allowing blood flow therethrough in said predetermined downstream direction, the locations of said eccentric axes shifting relative to said valve body in a downstream direction as said leaflets pivot to the open position,
   said leaflets each including a major body portion which is a section of a tube having a curved sidewall and being mounted with their concave surfaces facing each other in the open position and facing downstream in the closed position, said axes being located substantially upstream of the center of gravity of said leaflets when said leaflets are in the open position, and
   said valve body being formed with stop means exterior of said depressions which is positioned downstream of said location of said eccentric axes in said closed position.

15. A heart valve prosthesis comprising an annular valve body having a central passageway therethrough which is designed to be mounted to permit the flow of blood therethrough in a predetermined downstream direction, and
- a pair of leaflets which are supported by pairs of elongated guides in opposed elongated depressions upon said annular valve body for a substantially pivotal movement on eccentric axes between a closed position blocking blood flow through said central passageway and an open position allowing blood flow therethrough in said predetermined downstream direction, the locations of said eccentric axes shifting relative to said valve body in a downstream direction as said leaflets pivot to the open position,
- said leaflets each including a major body portion which is a section of a tube having a curved sidewall and being mounted with their concave surfaces facing each other in the open position and facing downstream in the closed position, said axes being located substantially upstream of the center of gravity of said leaflets when said leaflets are in the open position, and
- said depressions each having a straight edge along which said guide lies in the closed position, a straight edge along which said guide lies in the open position and an arcuate edge along which a downstream end of said guide travels as said leaflets pivot from the closed to the open position, said arcuate edge being located farther from a plane through the centerline of the passageway than said pivot axes.

16. A heart valve prosthesis comprising an annular valve body having a central passageway therethrough of substantially circular cross section which valve body is designed to be mounted to permit the flow of blood therethrough in a predetermined downstream direction, said valve body having seat means formed by a surface facing generally downstream, and
- a pair of leaflets which are supported upon said annular valve body for substantially pivotal movement on parallel eccentric axes between a closed position blocking blood flow through said central passageway and an open position allowing blood flow therethrough in said predetermined downstream direction,
- said leaflets each including a major body portion which is a section of a tube having an elliptical cross section and said leaflets being mounted with their concave surfaces facing each other, the curvature of said elliptical tubular section being chosen and said axes being located such that the downstream edge of each of said leaflets is substantially semi-circular, said downstream edge having a radius of curvature less than that of said seat means surface, whereby the curved edge of the leaflet in the closed position forms line contact with said seat surface and provides a close seal therewith.

17. A heart valve in accordance with claim 16 wherein said leaflets and said valve body include projecting guides and depressions which pivotally receive said guides.

18. A heart valve in accordance with claim 17 wherein said elliptical cross section is that of a 10° to 20° ellipse.

* * * * *

UNITED STATES PATENT AND TRADEMARK OFFICE
CERTIFICATE OF CORRECTION

PATENT NO. : 4,328,592
DATED : May 11, 1982
INVENTOR(S) : Jerome J. Klawitter

It is certified that error appears in the above—identified patent and that said Letters Patent is hereby corrected as shown below:

First page, Item 63, change "abandoned" to

U. S. Patent No. 4,308,624, issued January 5, 1982.

Column 11, line 62, "have" should read --has--.

Signed and Sealed this

Twenty-fourth Day of August 1982

|SEAL|

Attest:

GERALD J. MOSSINGHOFF

*Attesting Officer*   *Commissioner of Patents and Trademarks*

UNITED STATES PATENT AND TRADEMARK OFFICE

CERTIFICATE EXTENDING PATENT TERM
UNDER 35 U.S.C. 156

Patent No.    : 4,328,592

Dated         : May 11, 1982

Inventor(s)   : Jerome J. Klawitter

Patent Owner  : Hemex, Inc.

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

476 DAYS with all rights pertaining thereto as provided by 35 USC 156(b).

I have caused the seal of the Patent and Trademark Office to be affixed this First day of October 1987.

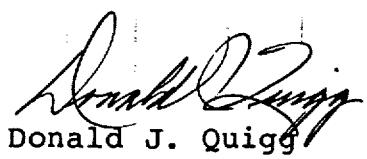

Donald J. Quigg

Assistant Secretary and Commissioner of Patents and Trademarks